United States Patent
Jin et al.

(10) Patent No.: US 10,983,057 B2
(45) Date of Patent: Apr. 20, 2021

(54) METHOD FOR PREPARING A RATIOMETRIC FLUORESCENT SENSOR FOR PARACETAMOL BASED ON A COPPER NANOCLUSTERS-CARBON DOTS-ARGININE COMPOSITE

(71) Applicant: Qingdao University, Qingdao (CN)

(72) Inventors: Hui Jin, Qingdao (CN); Rijun Gui, Qingdao (CN); Xiangning Bu, Qingdao (CN); Yongxin Fu, Qingdao (CN)

(73) Assignee: QINGDAO UNIVERSITY, Qingdao (CN)

( * ) Notice: Subject to any disclaimer, the term of this patent is extended or adjusted under 35 U.S.C. 154(b) by 0 days.

(21) Appl. No.: 16/622,284

(22) PCT Filed: Mar. 6, 2019

(86) PCT No.: PCT/CN2019/077071
§ 371 (c)(1),
(2) Date: Dec. 12, 2019

(87) PCT Pub. No.: WO2020/098182
PCT Pub. Date: May 22, 2020

(65) Prior Publication Data
US 2021/0010938 A1 Jan. 14, 2021

(30) Foreign Application Priority Data

Nov. 13, 2018 (CN) .......................... 201811342183.X

(51) Int. Cl.
*G01N 21/64* (2006.01)
*A61K 31/167* (2006.01)
*B82Y 5/00* (2011.01)

(52) U.S. Cl.
CPC ....... *G01N 21/6428* (2013.01); *A61K 31/167* (2013.01); *B82Y 5/00* (2013.01); *G01N 2021/6432* (2013.01)

(58) Field of Classification Search
None
See application file for complete search history.

(56) References Cited

U.S. PATENT DOCUMENTS 10,234,390 B2    3/2019   Voelcker

FOREIGN PATENT DOCUMENTS

| CN | 102519921 A | 6/2012 |
|---|---|---|
| CN | 102735729 A | 10/2012 |
| CN | 103482605 A | 1/2014 |
| CN | 104046353 A | 9/2014 |
| CN | 104694117 A | 6/2015 |
| CN | 106248766 A | 12/2016 |
| CN | 106872544 A | 6/2017 |
| CN | 106970061 A | 7/2017 |
| CN | 108489951 A | 9/2018 |
| CN | 109164083 A | 1/2019 |

OTHER PUBLICATIONS

Bu et al., Microchimica Acta (2020) 187: 154 , 1-10 (Year: 2020).*
Neijie He, et al., Ratiometric fluorescence and visual imaging detection of dopamine based on carbon dots/copper nanoclusters dual-emitting nanohybrids, Talanta, Sep. 9, 2017, pp. 109-115, 178.
Jinchun Song, et al., Graphite oxide film-modified electrode as an electrochemical sensor for acetaminophen, Sensors and Actuators B-Chemical, 2011, pp. 220-225, 155.
Arif Ul Alam, et al., Tailoring MWCNTs and B-Cyclodextrin for Sensitive Detection of Acetaminophen and Estrogen, American Chemical Society Appl. Mater. Interfaces, 2018, pp. 21411-21427, 10.
Li Ting, et al., Recent research in synthesis and application of copper nanoclusters, China Academic Journal Electronic Publishing House, Mar. 2016, vol. 36, No. 1.
Yunyun Qiao, et al., Green synthesis of fluorescent copper nanoclusters for reversible pH-sensors, Sensors and Actuators B: Chemical, Jun. 23, 2015, pp. 1064-1069, 220.

* cited by examiner

*Primary Examiner* — Andrea S Grossman
(74) *Attorney, Agent, or Firm* — Bayramoglu Law Offices LLC

(57) ABSTRACT

A method for preparing a ratiometric fluorescent sensor for paracetamol based on a copper nanoclusters-carbon dots-arginine composite is provided. Copper nanoclusters CuNCs with red fluorescence are bonded to carbon dots (CDs) with blue fluorescence by electrostatic adsorption and hydrogen bonding, and then arginine is added to form the CuNCs-CDs-arginine composite. The addition of arginine leads to a significant decrease in the blue fluorescence of the CDs, while after the paracetamol is added, the blue fluorescence of the CDs gradually recovered as a result of the specific binding of arginine to paracetamol. The ratiometric fluorescent sensor for paracetamol is constructed by taking the fluorescence of the CuNCs as a reference signal, and the fluorescence of the CDs as a response signal, and fitting the linear relationship between the ratios $I_{CDs}/I_{CuNCs}$ of fluorescence emission peak intensities of CDs and CuNCs and the molar concentrations of paracetamol.

5 Claims, 2 Drawing Sheets

METHOD FOR PREPARING A RATIOMETRIC FLUORESCENT SENSOR FOR PARACETAMOL BASED ON A COPPER NANOCLUSTERS-CARBON DOTS-ARGININE COMPOSITE

CROSS REFERENCE TO THE RELATED APPLICATIONS

This application is the national phase entry of International Application No. PCT/CN2019/077071, filed on Mar. 6, 2019, which is based upon and claims priority to Chinese Patent Application No. 201811342183.X, filed on Nov. 13, 2018, the entire contents of which are incorporated herein by reference.

TECHNICAL FIELD

The present disclosure belongs to the technical field of nanocomposite materials and fluorescence sensors preparation, and more particularly relates to a method for preparing a ratio metric fluorescent sensor for paracetamol based on a copper nanoclusters-carbon dots-arginine composite. The prepared sensor can be used for the highly sensitive and selectively quantitative detection of paracetamol.

BACKGROUND

Paracetamol, also known as acetaminophen, is a commonly used over-the-counter phenolic analgesic with anti-inflammatory and antipyretic effects. A small dose of paracetamol is beneficial to the human body, but overdose may cause health issues such as kidney failure, liver necrosis and the like. In fact, paracetamol overdose is one of the main causes of liver failure. Developing a simple, accurate and quantitative detection method for paracetamol in human serum is important for monitoring human health.

At present, there is increasing research on analytical techniques for the detection of paracetamol, including electrochemistry, colorimetry, chemiluminescence, fluorescence and other methods. Song et al. constructed a graphite oxide modified glass carbon electrode for electrochemical behavior determination of paracetamol (Jinchun Song, Ji Yang, Junfen Zeng, Juan Tan, Li Zhang. Graphite oxide film-modified electrode as an electrochemical sensor for acetaminophen. *Sensors and Actuators B-Chemical*, 2011, 155, 220-225). Alam et al. used β-Cyclodextrin where subject interacts with object and multi-walled carbon nanotubes with oxidation reduction property for the sensitive detection of trace paracetamol (Arif Ul Alam, Yiheng Qin, Massimo Catalano, Luhua Wang, Moon J. Kim, Matiar M. R. Howlader, Nan-Xing Hu, M. Jamal Deen. Tailoring MWCNTs and β-Cyclodextrin for Sensitive Detection of Acetaminophen and Estrogen. *ACS Applied Materials & Interfaces*, 2018, 10, 21411-21427).

Junhua Li et al. constructed an electrochemical sensor for paracetamol based on nanocomposite modified electrode (Junhua Li, Mengqin Liu, Fuxing Zhang, Zhifeng Xu, Peihong Deng, Siping Tang, Xing Liu. $CoFe_2O_4NWs$-RGO nanocomposite and paracetamol electrochemical sensor prepared based on $CoFe_2O_4NWs$-RGO nanocomposite. Chinese Invention Patent Publication No. CN106248766A). Xuecai Tan et al. reported a molecularly imprinted electrochemical analysis method for the determination of paracetamol (Xuecai Tan, Yuexin Sun, Huicheng Yu, Zaiyin Huang, Shaogang Liu, Fuhou Lei. Molecularly imprinted electrochemical sensor for paracetamol and preparation method thereof. Chinese Invention Patent Publication No. CN102735729A). Yaping Ding et al. constructed a fluorescent probe based on amino acid-modified CdTe nanoparticle for quantitative detection of paracetamol (Yaping Ding, Yaxiang Lu, Li Li, Liqiang Luo, Yu Cheng, Method for determining paracetamol by CdTe nano fluorescent probe. Chinese Invention Patent. Publication No. CN102519921A).

Methods of analysis and detection of paracetamol mainly include electrochemical analysis and fluorescence analysis. These methods only rely on a single signal output, which is susceptible to factors such as background, reagents, system and environmental conditions, resulting in fluctuations in measurement results. In contrast, employing the dual-signal ratio processing to obtain the intensity ratio of the signals achieves a self-calibration function, which effectively eliminates the interference of the autologous signal and the background signal and improves the accuracy and reliability of the detection results. In this regard, the present disclosure reports a ratiometric fluorescent sensor for paracetamol based on a copper nanoclusters-carbon dots-arginine composite. Copper nanoclusters CuNCs with red fluorescence are prepared by using DNA as a template, and bonded with carbon dots (CDs) with blue fluorescence by electrostatic adsorption and hydrogen bonding, and then arginine is added to form the CuNCs-CDs-arginine composite. The addition of arginine leads to a significant decrease in the blue fluorescence of the CDs. After the paracetamol is added, the blue fluorescence of the CDs gradually recovered as a result of the specific binding of arginine to paracetamol which causes separation of the arginine from the CDs. The addition of the arginine and the paracetamol do not significantly cause change in the fluorescence of the CuNCs. The ratiometric fluorescent sensor for paracetamol is constructed by taking the fluorescence of the CuNCs as a reference signal, and the fluorescence of the CDs as a response signal and fitting the linear relationship between the ratios $I_{CDs}/I_{CuNCs}$ of fluorescence emission peak intensities of the CDs and the CuNCs and the molar concentrations of paracetamol. Constructing the ratiometric fluorescent sensor based on a CuNCs-CDs-arginine composite and the ratiometric fluorescent method for detecting paracetamol has not been reported in domestic and foreign literatures and patents.

SUMMARY

The objective of the present disclosure is to overcome the deficiencies of the prior art described above, and design a method for preparing a ratiometric fluorescent sensor for paracetamol based on a copper nanoclusters-carbon dots-arginine composite, where the method is simple, low-cost, highly sensitive and selective.

In order to achieve the aforementioned objective, according to the present disclosure, a process of preparing the ratiometric fluorescent sensor for paracetamol based on the copper nanoclusters-carbon dots-arginine composite includes the following steps:

(1) preparation of CuNCs: dissolving DNA dry powder in ultrapure water to obtain a DNA solution, diluting the DNA solution to have the pH of 7.5 with the buffer solution containing 3-morpholine propane sulfonic acid and NaCl to obtain a DNA mixed solution, wherein concentrations of 3-morpholine propane sulfonic acid and NaCl are 10 mM and 15 mM, respectively; adding ascorbic acid to the DNA mixed solution, wherein the final concentration of the ascorbic acid is adjusted to 2 mM; at room temperature and stirred magnetically, adding $CuCl_2$ to the above DNA mixed solution, wherein the final concentration of the CuCl$_2$ is adjusted to 1 mM; performing a reaction on the mixed solution away from light for 20 minutes to obtain a product solution; dialyzing the product solution through a dialysis bag with the molecular weight cut-off of 1000 Da to remove unreacted experimental materials, pouring out the solution in the dialysis bag, removing 90% of the liquid by rotary evaporation, and then drying the remaining solution in vacuum to obtain the CuNCs; wherein the CuNCs are stored at 4° C. away from light, or dispersed in water to prepare a CuNCs aqueous dispersion for use;

(2) preparation of CDs: dissolving 1.5 g of deacetylated chitosan in 1.5 mL of acetic acid to mix well, adding 3 mL of polyvinyl amide, fully stirring for 10 minutes, adding 25.5 mL of double-distilled water to obtain a homogeneous dispersion; transferring the homogeneous dispersion into a miniature high-pressure reactor with a polytetrafluoroethylene liner, stirring to react at 200° C. for 5 hours; dialyzing the product solution through the dialysis bag with the molecular weight cut-off of 1000 Da to remove unreacted experimental materials, pouring out the solution in the dialysis bag, removing 90% of the liquid by rotary evaporation, and then drying the remaining solution in vacuum to obtain the CDs; wherein the CDs are stored at 4° C. away from light, or dispersed in water to prepare a CDs aqueous dispersion for use;

(3) preparation of CuNCs-CDs-arginine composite: under the magnetic stirring, adding the CDs aqueous dispersion into the CuNCs aqueous dispersion in a dropwise manner to form a homogeneous CuNCs-CDs mixture, then adding an aqueous solution of arginine into the homogeneous CuNCs-CDs mixture in a dropwise manner to form a homogeneous CuNCs-CDs-arginine composite solution;

(4) at room temperature and stirring magnetically, adding a certain dosage of paracetamol to the homogeneous CuNCs-CDs-arginine composite solution to form a homogeneous mixture, incubating the homogeneous mixture away from light for 5 minutes, measuring fluorescence emission spectra of the homogeneous mixture in the presence of different concentrations of paracetamol, fitting the linear relationship between the ratios $I_{CDs}/I_{CuNCs}$ of fluorescence emission peak intensities of the CDs and the CuNCs and the molar concentrations of paracetamol, constructing the ratiometric fluorescent sensor for paracetamol.

In step (1), the average size of the CuNCs with red fluorescence is 1-5 nm.

In step (2), the average size of the CDs with blue fluorescence is 1-5 nm.

In step (3), in the homogeneous mixture, the mass concentration of the CuNCs is 1-10 mg/mL, the mass concentration of the CDs is 1-10 mg/mL, the molar concentration of the arginine is 1-100 µM.

In step (4), the linear detection range of molar concentration of paracetamol is 0.01-500 µM, and the detection limit is 10-50 nM.

The present disclosure reports a ratiometric fluorescent sensor for paracetamol based on a copper nanoclusters-carbon dots-arginine composite. Copper nanoclusters CuNCs with red fluorescence are prepared by using DNA as template, and bonded to carbon dots (CDs) with blue fluorescence by electrostatic adsorption and hydrogen bonding, and then arginine is added to form the CuNCs-CDs-arginine composite. The addition of arginine leads to a significant decrease in the blue fluorescence of the CDs, while after the paracetamol is added, the blue fluorescence of the CDs gradually recovered as a result of the specific binding of arginine to paracetamol which causes separation of the arginine from the CDs. The addition of the arginine and the paracetamol do not significantly cause change in the fluorescence of the CuNCs. Taking the fluorescence of the CuNCs as reference signal, and the fluorescence of the CDs as response signal, by fitting the linear relationship between the ratios $I_{CDs}/I_{CuNCs}$ of fluorescence emission peak intensities of the CDs and the CuNCs and the molar concentrations of paracetamol, the ratiometric fluorescent sensor for paracetamol is constructed. Compared to the prior art, the method of the present disclosure has the advantages of easier operation, low cost, extensive resources of raw materials, strong anti-interference ability of the ratiometric signal, good accuracy, high sensitivity and high selectivity, which can be developed into a novel ratiometric fluorescent sensor for the efficient detection of paracetamol.

DETAILED DESCRIPTION OF THE EMBODIMENTS

The present disclosure will be further described below in conjunction with the drawings and specific embodiments.

Embodiment 1

Figure 1:
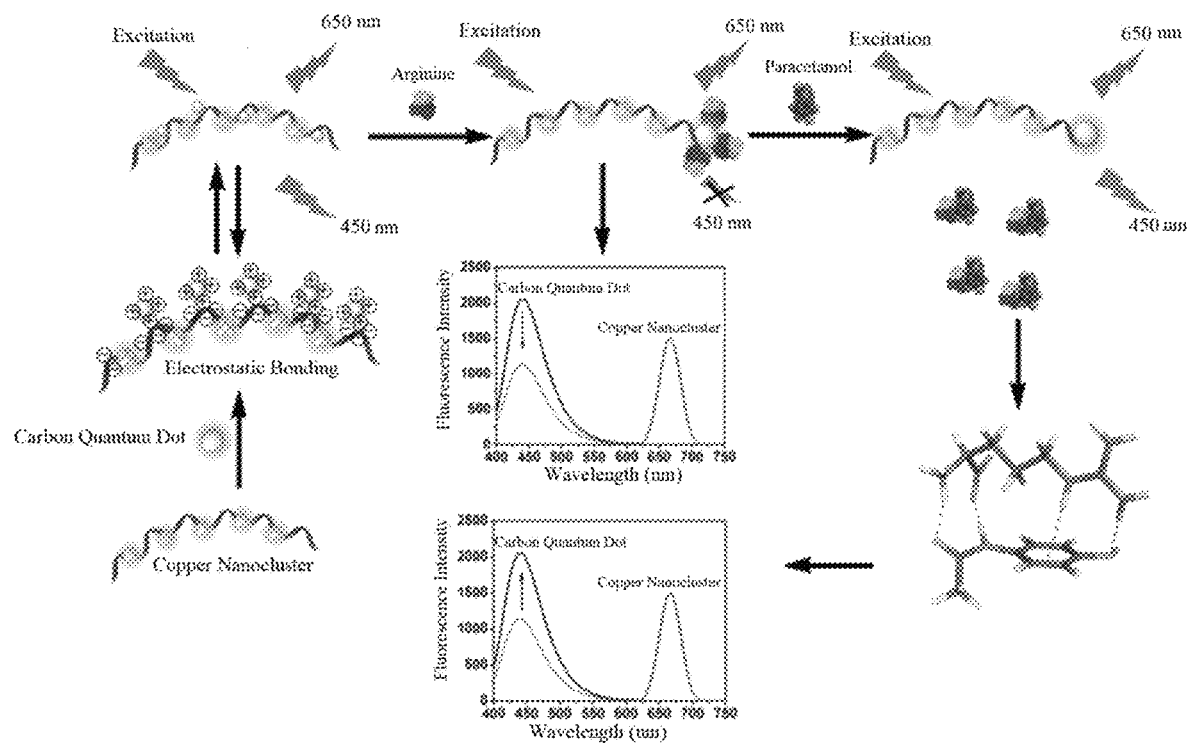
FIG. 1 is a schematic diagram showing the preparation for the ratiometric fluorescent sensor for paracetamol based on the copper nanoclusters-carbon dots-arginine composite and the principle of the detection of paracetamol of the present disclosure.

This embodiment relates to a method for preparing a ratiometric fluorescent sensor for paracetamol based on a copper nanoclusters-carbon dots-arginine composite. The preparation process of the ratiometric fluorescent sensor and the principle of the ratiometric fluorescent detection of paracetamol are shown in FIG. 1, and the specific process steps are as follows.

Preparation of CuNCs: DNA solution is obtained by dissolving DNA dry powder in ultrapure water and is diluted to have the pH of 7.5 with the buffer solution containing 3-morpholine propane sulfonic acid and NaCl, wherein concentrations of 3-morpholine propane sulfonic acid and NaCl are 10 mM and 15 mM, respectively. Ascorbic acid is added to the above DNA mixed solution, wherein the final concentration of the ascorbic acid is adjusted to 2 mM. At room temperature and stirred magnetically, CuCl$_2$ is added to the above DNA mixed solution in a dropwise manner, wherein the final concentration of the CuCl$_2$ is adjusted to 1 mM. The mixed solution reacts away from light for 20 minutes. The product solution is dialyzed through a dialysis bag with the molecular weight cut-off of 1000 Da to remove unreacted experimental materials. The solution in the dialysis bag is poured out and 90% of the liquid is removed by rotary evaporation, and then the remaining solution is dried in vacuum to obtain the CuNCs. The CuNCs are stored at 4°

C. away from light, or dispersed in water to prepare a CuNCs aqueous dispersion for use, wherein the average size of CuNCs is 2 nm.

Preparation of CDs: 1.5 g of deacetylated chitosan is dissolved in 1.5 mL of acetic acid to mix well, and 3 mL of polyvinyl amide is added. After fully stirring for 10 minutes, 25.5 mL of double-distilled water is added to obtain a homogeneous dispersion. The homogeneous dispersion is transferred into a miniature high-pressure reactor with a polytetrafluoroethylene liner and is stirred to react at 200° C. for 5 hours. The product solution is dialyzed through the dialysis bag with the molecular weight cut-off of 1000 Da to remove unreacted experimental materials. The solution in the dialysis bag is poured out and 90% of the liquid is removed by rotary evaporation, and then the remaining solution is dried in vacuum to obtain the CDs. The CDs are stored at 4° C. away from light, or dispersed in water to prepare a CDs aqueous dispersion for use, wherein the average size of CDs is 3 nm.

Preparation of CuNCs-CDs-arginine composite: under the magnetic stirring, the CDs aqueous dispersion is added into the CuNCs aqueous dispersion in a dropwise manner to form a homogeneous CuNCs-CDs mixture. Then, an aqueous solution of arginine is added into the homogeneous CuNCs-CDs mixture in a dropwise manner to form a homogeneous CuNCs-CDs-arginine composite solution, wherein the concentrations of the CuNCs, the CDs and the arginine are 5 mg/mL, 2 mg/mL and 50 µM, respectively.

Figure 2:
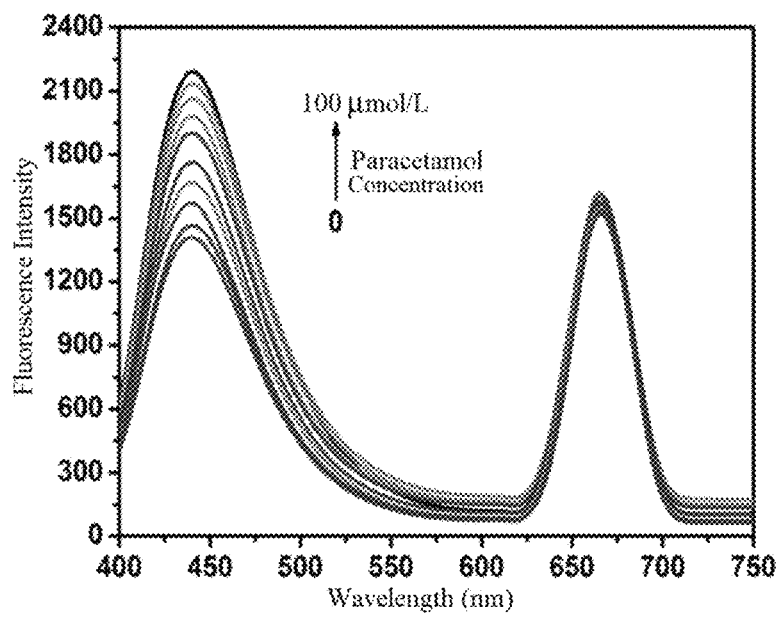
FIG. 2 shows the fluorescence emission spectra of sensor system corresponding to different molar concentrations of paracetamol measured by the ratiometric fluorescent sensor of the present disclosure.
Figure 3:
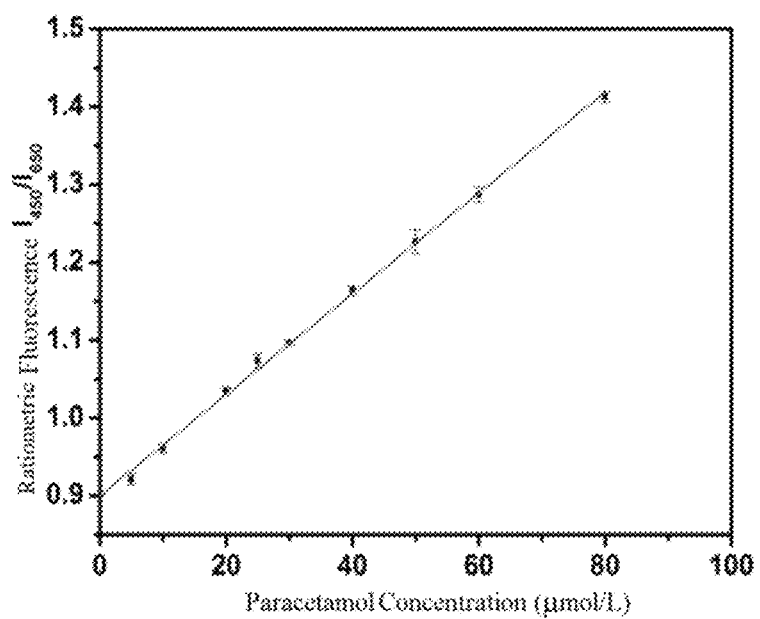
FIG. 3 shows the linear relationship between the ratios $I_{CDs}/I_{CuNCs}$ of fluorescence emission peak intensities of CDs and CuNCs and the different molar concentrations of paracetamol.

At room temperature and stirring magnetically, a certain dosage of paracetamol is added to the homogeneous CuNCs-CDs-arginine composite solution to form a homogeneous mixture. After incubating the homogeneous mixture away from light for 5 minutes, fluorescence emission spectra of the homogeneous mixture in the presence of different concentrations of paracetamol are measured (See FIG. 2). The ratiometric fluorescent sensor for paracetamol is constructed by fitting the linear relationship (See FIG. 3) between the ratios $I_{CDs}/I_{CuNCs}$ of fluorescence emission peak intensities of the CDs and the CuNCs and the molar concentrations of paracetamol, wherein the linear detection range of molar concentration of paracetamol is 0.02-400 µM, and the detection limit is 20 nM.

Embodiment 2 the schematic diagram of the preparation process of the ratiometric fluorescent sensor for paracetamol and the principle of the ratiometric fluorescent detection of paracetamol is the same as embodiment 1, and the process steps for preparing CuNCs and CDs are also the same as embodiment 1, wherein the average size of CuNCs is 3 nm and the average size of CDs is 4 nm. Other specific process steps are as follows.

Preparation of CuNCs-CDs-arginine composite: under the magnetic stirring, the CDs aqueous dispersion is added into the CuNCs aqueous dispersion in a dropwise manner to form a homogeneous CuNCs-CDs mixture. Then, an aqueous solution of arginine is added into the homogeneous CuNCs-CDs mixture in a dropwise manner to form a homogeneous CuNCs-CDs-arginine composite solution, wherein the concentrations of the CuNCs, the CDs and the arginine are 5 mg/mL, 5 mg/mL and 20 µM, respectively.

At room temperature and stirring magnetically, a certain dosage of paracetamol is added to the homogeneous CuNCs-CDs-arginine composite solution to form a homogeneous mixture. After incubating the homogeneous mixture away from light for 5 minutes, fluorescence emission spectra of the homogeneous mixture in the presence of different concentrations of paracetamol are measured. The ratiometric fluorescent sensor for paracetamol is constructed by fitting the linear relationship between the ratios $I_{CDs}/I_{CuNCs}$ of fluorescence emission peak intensities of the CDs and the CuNCs and the molar concentrations of paracetamol, wherein the linear detection range of molar concentration of paracetamol is 0.01-100 µM, and the detection limit is 10 nM.

Embodiment 3 the schematic diagram of the preparation process of the ratiometric fluorescent sensor for paracetamol and the principle of the ratiometric fluorescent detection of paracetamol is the same as embodiment 1, and the process steps for preparing CuNCs and CDs are also the same as embodiment 1, wherein the average size of CuNCs is 3 nm and the average size of CDs is 5 nm. Other specific process steps are as follows.

Preparation of CuNCs-CDs-arginine composite: under the magnetic stirring, the CDs aqueous dispersion is added into the CuNCs aqueous dispersion in a dropwise manner to form a homogeneous CuNCs-CDs mixture. Then, an aqueous solution of arginine is added into the homogeneous CuNCs-CDs mixture in a dropwise manner to form a homogeneous CuNCs-CDs-arginine composite solution, wherein the concentrations of the CuNCs, the CDs and the arginine are 2 mg/mL, 5 mg/mL and 10 µM, respectively.

At room temperature and stirring magnetically, a certain dosage of paracetamol is added to the homogeneous CuNCs-CDs-arginine composite solution to form a homogeneous mixture. After incubating the homogeneous mixture away from light for 5 minutes, fluorescence emission spectra of the homogeneous mixture in the presence of different concentrations of paracetamol are measured. The ratiometric fluorescent sensor for paracetamol is constructed by fitting the linear relationship between the ratios $I_{CDs}/I_{CuNCs}$ of fluorescence emission peak intensities of the CDs and the CuNCs and the molar concentrations of paracetamol, wherein the linear detection range of molar concentration of paracetamol is 0.02-500 µM, and the detection limit is 15 nM.

The above descriptions are only some of the preferred embodiments of the present disclosure. It should be noted that those skilled in the art can also make several improvements and modifications without departing from the principles of the present disclosure, and these improvements and modifications shall still fall within the protection scope of the present disclosure.

What is claimed is:

1. A method for preparing a ratiometric fluorescent sensor for paracetamol based on a copper nanoclusters-carbon dots-arginine composite (CuNCs-CDs-arginine composite), comprising:
    (1) preparing copper nanoclusters (CuNCs) by dissolving DNA dry powder in ultrapure water to obtain a DNA solution, diluting the DNA solution to a pH of 7.5 with a buffer solution containing 3-morpholine propane sulfonic acid and NaCl to obtain a DNA mixed solution, wherein a concentration of the 3-morpholine propane sulfonic acid is 10 mM and a concentration of the NaCl is 15 mM; adding ascorbic acid to the DNA mixed solution to obtain a first mixed solution, wherein a final concentration of the ascorbic acid is adjusted to 2 mM; at room temperature and stirred magnetically, adding $CuCl_2$ to the first mixed solution to obtain a second mixed solution, wherein a final concentration of the CuCl$_2$ is adjusted to 1 mM; performing a reaction on the second mixed solution away from light for 20 minutes to obtain a first product solution; dialyzing the first product solution through a dialysis bag with a molecular weight cut-off of 1000 Da to remove first unreacted experimental materials to obtain a first solution, pouring out the first solution in the dialysis bag and removing 90% of water in the first solution by a first rotary evaporation to obtain a first remaining solution, and then drying the first remaining solution in a vacuum to obtain the CuNCs; wherein the CuNCs are stored at 4° C. away from light, or dispersed in water to prepare a CuNCs aqueous dispersion for use;

(2) preparing carbon dots (CDs) by dissolving and mixing 1.5 g of deacetylated chitosan in 1.5 mL of acetic acid to obtain a third mixed solution, adding 3 mL of polyvinyl amide to the third mixed solution to obtain a fourth mixed solution, stirring the fourth mixed solution for 10 minutes, adding 25.5 mL of double-distilled water to the fourth mixed solution to obtain a homogeneous dispersion; transferring the homogeneous dispersion into a miniature high-pressure reactor with a polytetrafluoroethylene liner, stirring the homogeneous solution to react at 200° C. for 5 hours to obtain a second product solution; dialyzing the second product solution through the dialysis bag with the molecular weight cut-off of 1000 Da to remove second unreacted experimental materials to obtain a second solution, pouring out the second solution in the dialysis bag and removing 90% of water in the second solution by a second rotary evaporation to obtain a second remaining solution, and then drying the second remaining solution in a vacuum to obtain the CDs; wherein the CDs are stored at 4° C. away from light, or dispersed in water to prepare a CDs aqueous dispersion for use;

(3) preparing the CuNCs-CDs-arginine composite by, while using a magnetic stirrer, adding the CDs aqueous dispersion into the CuNCs aqueous dispersion in a dropwise manner to form a homogeneous CuNCs-CDs mixture, then adding an aqueous solution of arginine into the homogeneous CuNCs-CDs mixture in a dropwise manner to form a homogeneous CuNCs-CDs-arginine composite solution; and (4) at room temperature and stirring magnetically, adding the paracetamol with a plurality of molar concentrations to the homogeneous CuNCs-CDs-arginine composite solution to form a plurality of homogeneous mixtures, incubating the plurality of homogeneous mixtures away from light for 5 minutes, measuring fluorescence emission spectra of the plurality of homogeneous mixtures, wherein in each of the fluorescence emission spectra, a fluorescence emission peak intensity of the carbon dots is $I_{CDs}$, a fluorescence emission peak intensity of the copper nanoclusters is $I_{CuNCs}$, fitting a linear relationship between ratios $I_{CDs}/I_{CuNCs}$ of fluorescence emission peak intensities of the CDs and the CuNCs and the plurality of molar concentrations of the paracetamol, thereby constructing the ratiometric fluorescent sensor for the paracetamol.

2. The method for preparing the ratiometric fluorescent sensor for the paracetamol based on the copper nanoclusters-carbon dots-arginine composite according to claim 1, wherein, in step (1), an average size of the CuNCs is 1-5 nm, and the CuNCs emit red fluorescence.

3. The method for preparing the ratiometric fluorescent sensor for the paracetamol based on the copper nanoclusters-carbon dots-arginine composite according to claim 1, wherein, in step (2), an average size of the CDs is 1-5 nm, and the CDs emit blue fluorescence.

4. The method for preparing the ratiometric fluorescent sensor for the paracetamol based on the copper nanoclusters-carbon dots-arginine composite according to claim 1, wherein, in step (3), in the homogeneous CuNCs-CDs-arginine composite solution, a mass concentration of the CuNCs is 1-10 mg/mL, a mass concentration of the CDs is 1-10 mg/mL, a molar concentration of the arginine is 1-100 μM.

5. The method for preparing the ratiometric fluorescent sensor for the paracetamol based on the copper nanoclusters-carbon dots-arginine composite according to claim 1, wherein, in step (4), a linear detection range of the molar concentrations of the paracetamol is 0.01-500 μM, and a detection limit of the molar concentrations of the paracetamol is 10-50 nM.

* * * * *